United States Patent [19]

Soderquist et al.

[11] 4,039,601

[45] Aug. 2, 1977

[54] PROCESS AND APPARATUS FOR CONTINUOUS CATALYST ACTIVATION

[75] Inventors: Frederick J. Soderquist, Essexville; Theodore T. Wazbinski, Bay City; Nathan Waldman, Midland, all of Mich.

[73] Assignee: The Dow Chemical Company, Midland, Mich.

[21] Appl. No.: 698,667

[22] Filed: June 22, 1976

[51] Int. Cl.$^2$ .............................................. C07C 15/00
[52] U.S. Cl. ............................... 260/669 R; 252/420; 23/288 B
[58] Field of Search ...................... 260/669 R; 252/420

[56] References Cited

U.S. PATENT DOCUMENTS 3,907,916  9/1975  Soderquist et al. ............... 260/669 R Primary Examiner—Delbert E. Gantz
Assistant Examiner—Joseph A. Boska
Attorney, Agent, or Firm—Glwynn R. Baker

[57] ABSTRACT

Self-regenerative catalysts for dehydrogenating an alkylaromatic hydrocarbon to the corresponding alkenylaromatic hydrocarbon are continuously activated by steaming successive small portions of the catalyst bed during normal operation. Each small portion of the catalyst bed is steamed for about 7–30 minutes at least once every 24 hours by a separate small steam inlet which during the activation period admits a flow of steam sufficient to exclude hydrocarbon feed from that portion of the bed. The process is applicable to both heated case reactors and to adiabatic reactors using packed or radial beds. Reactors adapted for use of the process are described.

4 Claims, 5 Drawing Figures

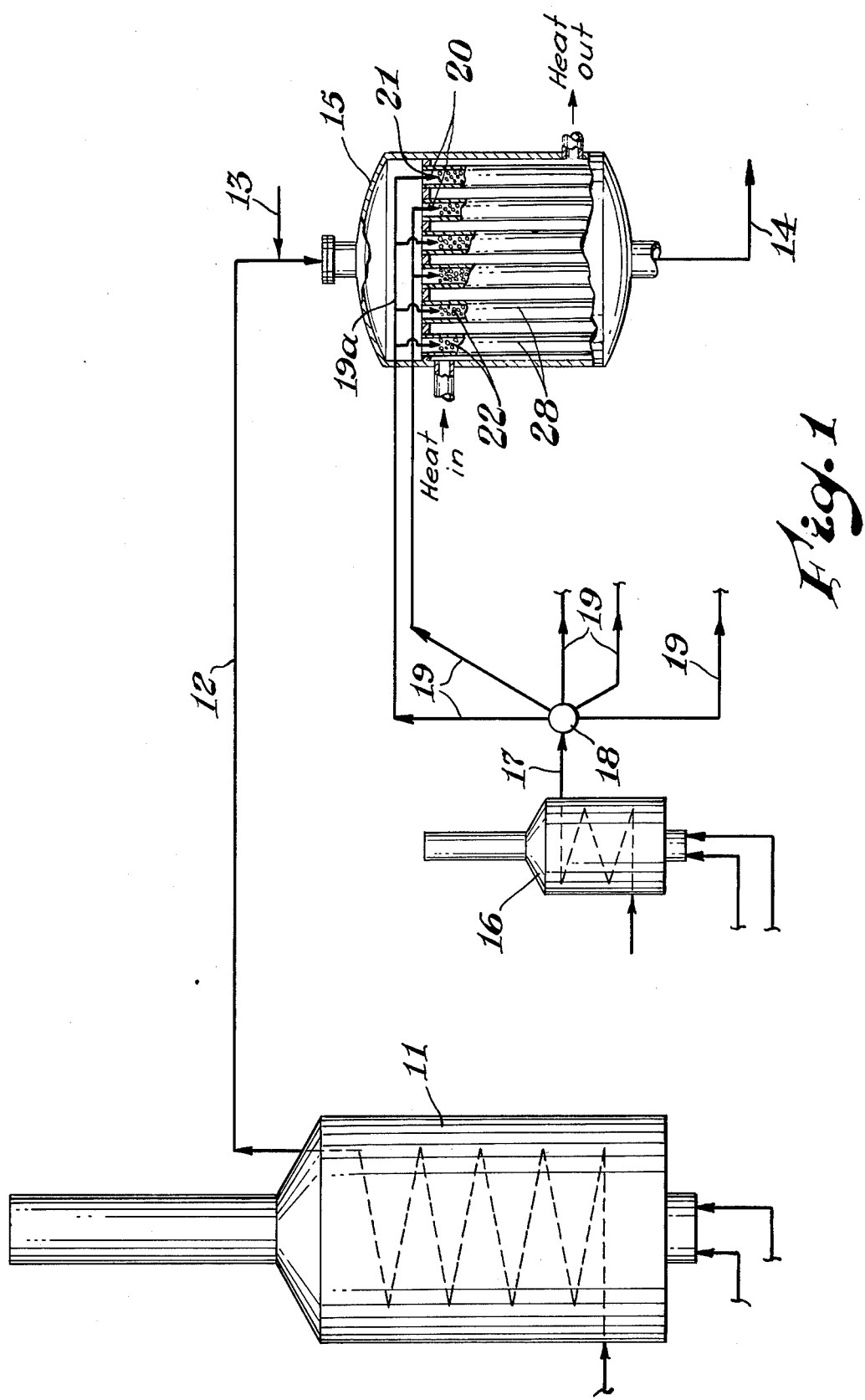

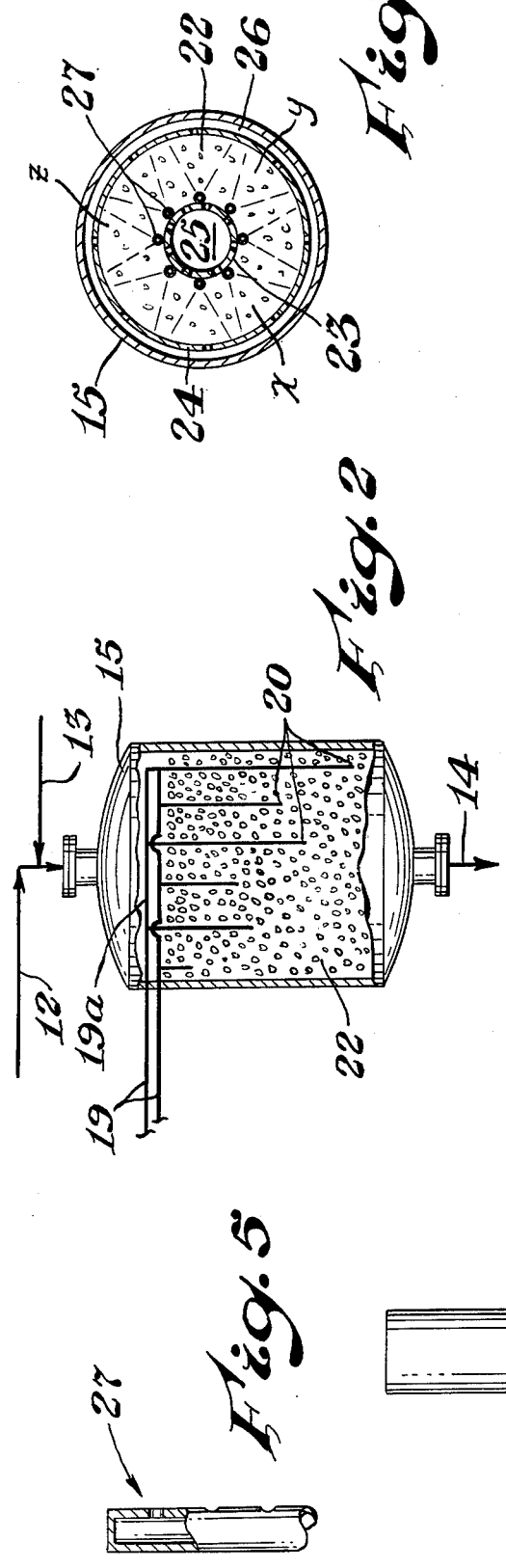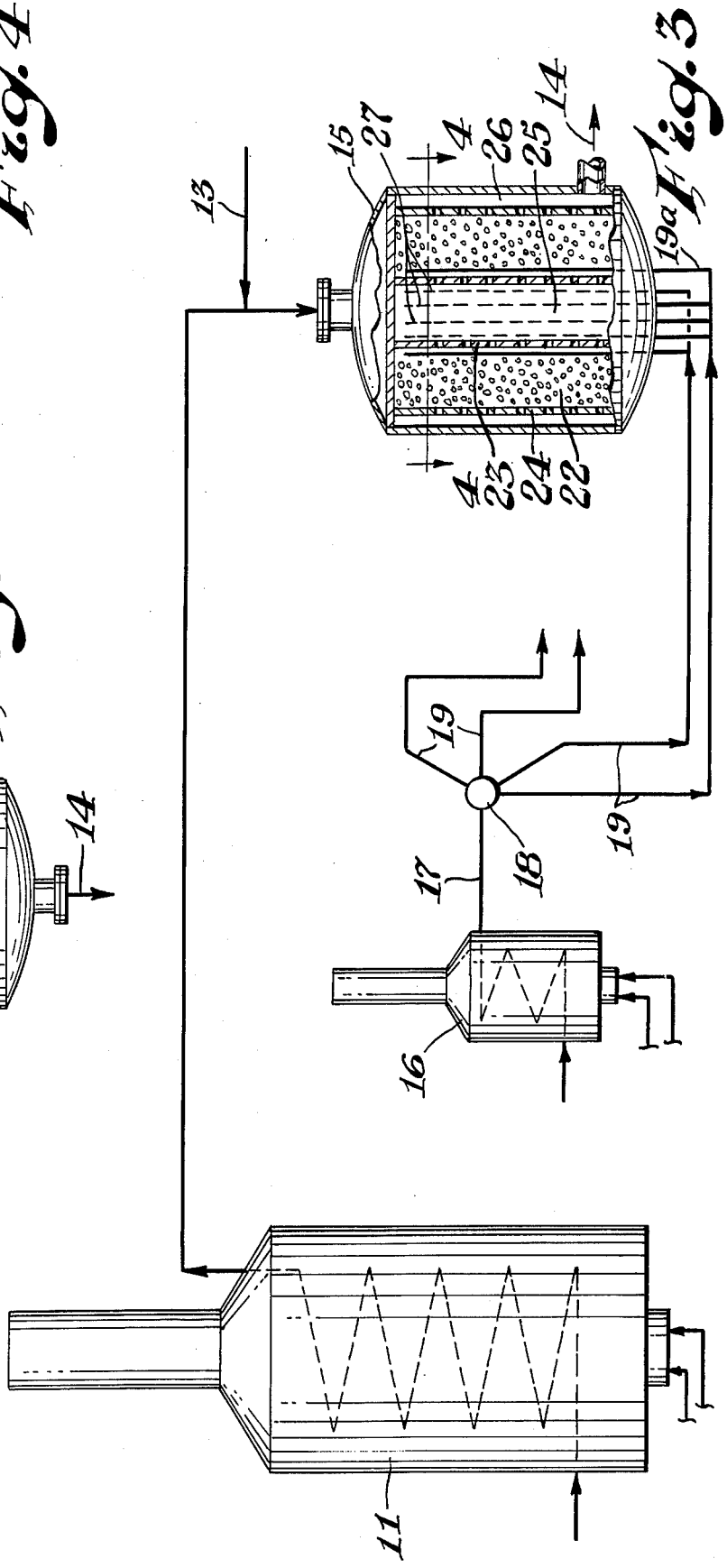

PROCESS AND APPARATUS FOR CONTINUOUS CATALYST ACTIVATION

BACKGROUND OF THE INVENTION

Dehydrogenation of alkyl aromatic hydrocarbons, such as ethyl benzene to styrene, ethyl toluene to vinyl toluene, diethyl benzene to a mixture of divinyl benzene and vinyl ethyl benzene, isopropyl benzene to isopropenyl benzene, and ethyl naphthalene to vinyl naphthalene, by passing a mixture of steam and such alkyl aromatic hydrocarbon over a "self-regenerative" catalyst is known. The self-regenerative catalysts are usually described as those containing one or more oxides of iron, zinc, chromium or magnesium, as the major ingredient, and an alkali metal oxide, hydroxide or carbonate, particularly potassium or rubidium oxides, hydroxides or carbonates, as water gas reaction promoting ingredients. This reaction tends to mitigate carbon build-up on the catalyst surface, thereby permitting long periods of continuous dehydrogenation cycles for converting alkyl aromatic hydrocarbons having at least one alkyl group of 2 to 3 C atoms to the corresponding alkenyl aromatic hydrocarbon. Representative self-regenerative catalysts are disclosed in U.S. Pat. Nos. 2,370,797, 2,395,875, 2,414,585, 2,426,829, 2,461,147, 3,205,179 and 3,703,593. These catalysts usually contain one or more of the oxides of iron, zinc, chromium or magnesium as the major ingredient and an alkali metal oxide, hydroxide or carbonate, preferably the potassium compound, as a water gas reaction promoting ingredient. The catalysts may also contain other additives such as stabilizers, binders and porosity control agents. These additives are known in the art and are described in the above-cited patents.

In our U.S. Pat. No. 3,907,916 it is demonstrated that a self-regenerative catalyst which consists essentially of a major proportion of at least one oxide of iron, zinc, chromium or magnesium, and which also contains an amount of an alkali metal oxide, hydroxide, or carbonate, preferably the potassium compounds, to promote the water gas reaction, a chromium compound as a promoter, and, optionally, a stabilizer, binders and/or porosity control agents, can be activated by short, periodic steaming cycles (without presence of alkyl aromatic hydrocarbon). A steaming cycle of about 7-30 minutes every 24-48 hours at a temperature of from about 600° C to about 700° C, is sufficient to activate the catalysts. Most conveniently the previous operating temperature is used for activation.

Activation of the catalyst apparently is not due to decoking, because little or no carbon oxides are found in the effluent during the activation cycle.

After activation, the conversion of alkyl aromatic hydrocarbons to alkenyl derivatives is increased, the selectivity remains high and the dehydrogenation cycle can be run under high severity conditions, e.g., low steam to hydrocarbon ratios or higher temperatures or both without excessive coking of the catalyst. It is thus possible to attain increased throughput per reactor and also to obtain higher yields of alkenyl aromatic hydrocarbon at lower reaction temperatures.

Although that activation process is highly effective as shown in the examples of U.S. Pat. No. 3,907,916, it has certain disadvantages when used as described in large scale plant operation. These disadvantages include pressure surges when the hydrocarbon feed is abruptly terminated and restarted, the relatively long time required to purge the whole apparatus, and the consequent difficulty of determining the actual catalyst purge time. In addition, it has been found necessary to substitute some steam condensate for the hydrocarbon feed during the short steam activation cycle to prevent excessive temperatures from developing in the heat exchange system.

SUMMARY OF THE INVENTION

It has been found that these disadvantages are largely or entirely avoided in fixed bed reactors by applying the steam activation procedure portionwise, that is, to successive small portions of the catalyst bed while the rest of the bed is operating normally in the dehydrogenation process. In essence, the invention constitutes a way of terminating the flow of alkylaromatic feed only to small sections of the catalyst bed and activating these sections while the flow of alkylaromatic hydrocarbon continues through the major portion of the catalyst bed. This improvement comprises activating the whole catalyst bed in successive small parts by applying a separate stream of activating steam to a first minor portion of the bed in a flow sufficient to exclude substantially all of the alkylaromatic hydrocarbon feed to that first minor portion only, maintaining the stream of activating steam to said first minor portion of catalyst bed in that manner for about 7-30 minutes, then discontinuing the stream of activating steam to that first minor portion of bed, thereby allowing the resumption of alkylaromatic hydrocarbon plus process steam thereto, subsequently applying another separate stream of activating steam to a second minor portion of the catalyst bed in the same fashion and repeating this portionwise activating process until each minor portion of the catalyst bed has been so activated at least once in 24 hours.

The invention is also defined by the various types of fixed bed reactor adapted to the portionwise steam activation process by having a plurality of individually operated activating steam outlets so disposed that each minor portion of the catalyst bed is separately purged by steam from its own activation steam outlet while normal dehydrogenation proceeds in the remaining portions of the bed.

DESCRIPTION OF THE DRAWINGS

The various aspects of the invention are more readily understood by reference to the drawings.

FIG. 1 shows a heated case or tube and shell reactor supplied with process steam from a process steam superheater and with activation steam from a smaller superheater, the activation steam being distributed by multiple, separately operable lines to different sets of catalyst tubes.

FIGS. 2 and 3 show an older type of packed bed adiabatic reactor and a more recently developed radial or axial flow adiabatic reactor respectively. The reactor of FIG. 2 has multiple sets of separately operable activation steam inlet pipes extending to various positions within the catalyst bed.

FIG. 3 illustrates a radial flow reactor where similar portionwise activation is provided by separately operable perforated steam pipes vertically disposed around the central core inlet.

FIG. 4 is a cross section along lines 4—4 of FIG. 3.
FIG. 5 is a detail section from FIGS. 3 and 4 showing the closed end and side perforations in an activation steam inlet pipe.

It is to be understood that the drawings illustrate certain specific embodiments of the invention and other such embodiments differing in detail from these are possible. For example, a separate superheater for the activation steam is not necessarily required, the process stream inlet can be at the bottom of the reactor, instead of the top, and so on. The scope of the invention is limited only by the appended claims.

DETAILED DESCRIPTION

Referring to FIG. 1 of the drawings, a mixture of superheated steam via line 12 from the process steam superheater 11 and vaporized alkylaromatic plus steam via line 13 is introduced into the reactor 15 and passes through the catalyst 22 which is contained in a number of catalyst tubes 28 externally heated by hot flue gas or other such hot gas. The dehydrogenated product and steam leaves the reactor via an outlet line 14 for condensation and separation of the components. At predetermined intervals during the dehydrogenation process, activation steam at about process temperature from activation steam superheater 16 via line 17 is directed by distributing valve 18 to one or more of a number of activation steam inlet lines 19, each feeding a manifold 19a having several outlets 20, each of which is disposed above and opposed to an upper or inlet open end 21 of a catalyst tube 28. Each manifold 19a supplies several outlet ends 20 so that a corresponding number of catalyst tubes 28 constituting a set more or less evenly distributed within the reactor can be purged with activating steam without concentrating any activation-caused temperature difference in one section of the reactor.

FIG. 2 illustrates the application of the process to an adiabatic reactor containing a packed bed of catalyst wherein the reactor temperature is controlled essentially by the superheated process steam entering through line 12 and the reactor 15 is essentially a hollow cylinder largely filled with bulk catalyst 22. In this mode of the invention, the activation steam manifold outlets 20 are distributed in the bed of catalyst substantially evenly disposed at various depths throughout the bed in such a pattern that any particular small section of catalyst bed is subject to activation steam purge by one of those outlets. As in FIG. 1, each activation steam manifold 19a has outlet ends 20 spaced apart to purge various separate areas to avoid concentrating the activation in any one section of the catalyst bed.

FIG. 3 with FIGS. 4 and 5 illustrates another mode of using the invention in a different kind of adiabatic reactor wherein the catalyst 22 is contained as an annular or ring shaped bed between inner (23) and outer (24) concentric cylindrical screens or perforated sheets. Process steam and hydrocarbon feed vapor from lines 12 and 13 respectively enter the open axial core 25 and proceed radially through the inner screen 23 and catalyst bed 22 to the annular space 26 between the outer screen 24 and the outside wall of the reactor 15 and thence through outlet line 14 to condensation and separation facilities. In this mode of the invention, activation steam is provided by inlet lines 19, each connected to a manifold 19a with outlet pipes 27 vertically disposed in or along the catalyst bed adjacent to the inner screen 23, said pipes having closed ends and containing perforations along their length facing toward the nearest point on the outer surface of the catalyst bed so that activation steam flows from an outlet pipe through a wedge-shaped section x, y, z of the catalyst bed and through the outer screen 24 and mixes with the general dehydrogenation process stream, see FIG. 4 and detail in FIG. 5 of outlet pipe end.

In all modes of the invention, activation steam is passed through predetermined sections of the catalyst bed in activation cycles of about 7-30 minutes spaced in such a way that each section of catalyst bed is subjected to at least one such cycle in each 24 hours of operation. While one steam activation per 24 hour process cycle has been found to be enough to maintain the activity of the catalyst at a desirably high level, the range of fluctuation of catalyst activity is reduced and undesirable sharp peaks of activity upon reactivation are avoided in most cases by applying activation steam to each section of catalyst two or three times in each 24 hour period, i.e., once every 8-12 hours of process time. In this way, conversion and selectivity are maintained at essentially even levels near their optimum values and byproduct formation resulting from sharp activity peaks in newly activated sections of catalyst is minimized. In each mode of the invention as illustrated above, the activation steam flow is adjusted so that it is sufficient to exclude substantially all hydrocarbon feed from the section of catalyst being purged during the activation cycle but limited in such a way that the amount of activation steam is not significantly in excess of that flow and adjacent sections of catalyst bed are not appreciably affected. By use of this invention, it is thus possible to run the dehydrogenation process continuously in a reactor with a major portion of the catalyst bed engaged in active dehydrogenation at any one time and only a small minor portion of catalyst being purged with activation steam. Since only a minor portion of the total catalyst is being activated at any time, the amount of activation steam is also minor compared to the amount of process steam so that the ratio of total steam to hydrocarbon is not substantially greater than the ratio of steam to hydrocarbon used in normal dehydrogenation. The dehydrogenating activity of all of the catalyst is thereby maintained at or near its optimum level throughout the process without need for periodic shutting off and then restarting the hydrocarbon flow through the reactor.

In commercial single stage reactors the available self-regenerative catalysts have functioned satisfactorily at comparatively high steam to alkyl aromatic hydrocarbon ratios and at conversions of about 38 percent or slightly higher. The steam ratio will vary somewhat depending on the particular alkyl aromatic hydrocarbon undergoing dehydrogenation.

Representative alkyl aromatic hydrocarbons and ranges of steam to hydrocarbon ratios of the processes of the prior art are tabulated below.

TABLE I

| Hydrocarbon | Steam/Hydrocarbon Ratio |
|---|---|
| Ethylbenzene | 2.6 to 1 to 2.0 to 1 |
| Ethyltoluene | 5 to 1 to 3 to 1 |
| Diethylbenzene | 8 to 1 to 3 to 1 |
| Isopropylbenzene | 3 to 1 to 2 to 1 |

When the catalysts are activated by periodic steaming for 7 to 30 minutes as disclosed herein, suitable ratios are as follows:

TABLE II

| Hydrocarbon | Steam/Hydrocarbon Ratio |
|---|---|
| Ethylbenzene | 1 to 1 to 0.4 to 1 |
| Ethyltoluene | 3 to 1 to 1.5 to 1 |
| Diethylbenzene | 6 to 1 to 1.5 to 1 |
| Isopropylbenzene | 1.5 to 1 to 0.4 to 1 |
| Ethyl naphthalene | 1.5 to 1 to .4 to 1 |
| Ethyl biphenyl | 2 to 1 to .8 to 1 |

Usually, the effect of the above-defined steam activation of catalyst is not apparent if the steam: hydrocarbon ratios are increased appreciably above the maximum values given in Table II.

Although all the self-regenerative catalysts tested have responded to the activation procedure, the degree of response is not uniform for each such catalyst. In general, the greatest degree of desirable activation was found with catalysts containing approximately equal amounts by weight of ferric and zinc oxides containing from about 5 to about 30 percent by weight of potassium oxide, hydroxide or carbonate, from about 5 to about 10 weight percent of a copper, cadmium, thorium or silver oxides, from about 5 to 10 weight percent of alkali metal chromate, a minor amount 1 to 5 percent of a refractory type cement, and a minor amount of carbonaceous material such as methyl cellulose ethers, graphite or other ingredients defined in U.S. Pat. No. 3,205,179.

A representative catalyst made by the procedure of U.S. Pat. No. 3,205,179 contained the following.

| Ingredient | Weight Percent |
| --- | --- |
| $Fe_2O_3$ | 24.81 – 30.0 |
| ZnO | 24.81 – 30.0 |
| $K_2CO_3$ | 9 – 22.5 |
| $Cu_2O$ | 7.44 – 9.0 |
| $Na_2Cr_2O_7$ | 7.44 – 9.0 |
| Alumina (low silica) Cement | 3.90 |
| Methyl Cellulose | 4.00 |
| Graphite | 5.10 |

Other catalysts which are especially responsive to the activation procedure are those which are made from a mixture of hydrated (yellow) iron oxide and anhydrous (red) iron oxide in a weight ratio of 1:4 to 17:20 and about 13:7 to 4:1, respectively. These catalysts and their methods of preparation are described in U.S. Pat. No. 3,703,593. A representative catalyst had the following composition. $Fe_2O_3 + Fe_2O_3 \cdot H_2O$ 58.9 percent, $K_2CO_3$ 16.7 percent, $K_2Cr_2O_7$ 2.5 percent, $V_2O_5$ 2.5 percent, methyl cellulose 8.3 percent, graphite 8.3 percent, cement 2.8 percent.

Other catalysts which are activated so that they perform better under high severity reaction conditions (e.g., low steam:hydrocarbon ratio or high temperature or both) include those having the following compositions.

| Component | Weight Percent | | | | |
| --- | --- | --- | --- | --- | --- |
| | I | II | III | IV | V |
| $Fe_2O_3$ | 74.5 | 83.0 | 87.9 | 71.9 | 62.5 |
| $Cr_2O_3$ | 2.0 | 2.2 | 2.5 | 2.3 | 2.2 |
| $K_2O$ | — | — | 9.6 | — | — |
| $K_2CO_3$ | 20.0 | 14.8 | — | 25.8 | 35.3 |
| $V_2O_5$ | 3.5 | — | — | — | — |

The steam to hydrocarbon ratio during the dehydrogenation cycle is within the ranges defined in Table II above.

What is claimed is:

1. In the method of activating a bed of self-regenerative dehydrogenation catalyst during the dehydrogenation of an alkyl aromatic hydrocarbon having from 1 to 2 six membered rings and from 1 to 2 alkyl groups of 2-3 carbon atoms to the corresponding alkenyl aromatic hydrocarbon by passing a mixture of process steam and said alkyl aromatic hydrocarbon over said catalyst at about 600° to about 700° C wherein the method of activating comprises periodically interrupting the feed of alkyl aromatic hydrocarbon and continuing the feed of process steam at said temperature for about 7-30 minutes to provide a catalyst activation cycle and then resuming the feed of said alkyl aromatic hydrocarbon for dehydrogenation thereof under high severity reaction conditions, the improvement wherein a plurality of minor portions of said catalyst bed are individually and successively activated in a portionwise activating process by applying to a first minor portion of catalyst bed a separate stream of activating steam in a flow sufficient to exclude substantially all of the alkylaromatic hydrocarbon feed to that first minor portion only, maintaining the stream of activating steam to said first minor portion in that manner for about 7-30 minutes, then discontinuing the stream of activating steam to said first minor portion of catalyst bed, thereby allowing the resumption of alkylaromatic hydrocarbon feed thereto, subsequently applying a separate stream of activating steam to a second minor portion of the catalyst bed in the same fashion and repeating the above portionwise activating process until each minor portion of the catalyst bed has been so activated at least once in 24 hours.

2. The method of claim 1 wherein the catalyst bed is subjected to the portionwise activating process once in about 8-12 hours.

3. The method of claim 1 wherein the catalyst consists essentially of about equal amounts of ferric oxide and zinc oxide, about 5-30 percent by weight of potassium oxide, hydroxide, or carbonate, about 5-10 percent of an oxide of copper, cadmium, thorium, or silver, and about 5-10 percent of alkali metal chromate.

4. The method of claim 1 wherein the catalyst consists essentially of a mixture of hydrated iron oxide and anhydrous iron oxide and minor amounts of potassium carbonate, an alkali metal chromate, and vanadium oxide.

* * * * *